US005779639A

United States Patent [19]

Yeung

[11] Patent Number: 5,779,639
[45] Date of Patent: Jul. 14, 1998

[54] ULTRASOUND PROBE WITH OFFSET ANGLE TIP

[75] Inventor: Hubert K. Yeung, Lynnfield, Mass.

[73] Assignee: Hewlett-Packard Company, Palo Alto, Calif.

[21] Appl. No.: 754,489

[22] Filed: Nov. 21, 1996

[51] Int. Cl.$^6$ ........................................ A61B 8/00
[52] U.S. Cl. ............................................ 600/446
[58] Field of Search ................. 128/660.1, 662.03, 128/662.06; 600/446, 459, 463

[56] References Cited

U.S. PATENT DOCUMENTS

| | | | |
|---|---|---|---|
| 4,385,255 | 5/1983 | Yamaguchi et al. | 310/335 |
| 4,494,548 | 1/1985 | Buon et al. | 128/660 |
| 4,535,781 | 8/1985 | Hetz | 128/660 |
| 4,543,960 | 10/1985 | Harui et al. | 128/660 |
| 4,582,066 | 4/1986 | Barnes et al. | 128/661 |
| 4,898,177 | 2/1990 | Takano et al. | 128/662.03 |
| 5,070,881 | 12/1991 | Weiland | 128/662.03 |
| 5,255,684 | 10/1993 | Rello | 128/662.06 |
| 5,284,147 | 2/1994 | Hanaoka et al. | 128/662.06 |
| 5,299,578 | 4/1994 | Rotteveel et al. | 128/662.06 |
| 5,381,795 | 1/1995 | Nordgren et al. | 128/663.01 |
| 5,400,790 | 3/1995 | Pohan et al. | 128/662.06 |

*Primary Examiner*—Francis Jaworski

[57] ABSTRACT

An ultrasound imaging probe having connected tip and handle regions with longitudinal axes that intersect each other at an acute angle. An ultrasonic transducer opposes a patient-contacting surface at a distal end of the tip region and is positioned orthogonal to that region's axis. This novel shape enables the administering sonographer to position the probe at the suprasternal window without substantially tilting the probe and without requiring a substantial adjustment of the patient's head, thereby obtaining improved cardiac imaging of pediatric patients and others who cannot steadily hold their head in a backwardly tilted position to accommodate the placement of conventional ultrasonic probes. In addition, the shape allows for the unassisted positioning of the probe within the subcostal window. The ultrasound transducer is a phased-array transducer rotational about the tip region axis. An angled drive shaft having a universal joint axially drives the transducer about the tip region axis with minimal rotational forces, resulting in a probe having a minimal number of lightweight parts associated with the rotation of the transducer. Advantageously, this enables the probe to be used to obtain multiple images from the same perspective without having to adjust the position of the probe on the patient. A strain-relief connector assembly having a flex circuit, an angled flex circuit holder and an energy-absorbing coax bundle provide electrical connections about the periphery of the probe between a cable at the proximal end of the handle region and the ultrasound transducer at the distal end of the structure. As the flex circuit and flex circuit holder rotate with the transducer, the holder maintains a secure connection between the coax bundle and flex circuit while the coax bundle absorbs the energy associated with the rotation.

19 Claims, 5 Drawing Sheets

ULTRASOUND PROBE WITH OFFSET ANGLE TIP

BACKGROUND OF THE INVENTION

1. Field of the Invention

The present invention relates generally to ultrasonic probes and, more particularly, to transthoracic ultrasound imaging probes.

2. Related Art

Ultrasonic imaging of anatomical structures is a diagnostic technique used to observe and monitor a patient's condition during surgical and other procedures. With this technique, ultrasonic energy is transmitted into a body resulting in the reflection of energy from boundaries of fluids, organs, tissues and other anatomical structures. This reflected energy is intercepted, typically by a transducer, and its informational content is extracted and processed, providing an indication of the patient's condition. Ultrasonic imaging is commonly used to observe a wide range of physical conditions and to identify many types of disorders. For example, it is employed in prenatal examinations of a fetus, in the monitoring of conditions during surgical procedures, and in the measurement of cardiac structures and functions. This latter approach, which is of significance in the present application, is referred to as echocardiography.

Various techniques have been developed for ultrasound cardiac imaging. Some conventional methods include invasive steps in which there is some disruption or alteration of the vascular and/or cardiac systems. Other conventional methods are directed to imaging the heart during surgical operations when the heart is exposed. These invasive approaches are limited in their application for a variety of reasons, including patient discomfort, increased risk of complications, and the need to use sterilized and expensive medical devices.

Non-invasive echocardiographic methods also exist. Conventional transthoracic ultrasound imaging probes have been developed for this purpose because surgical imaging probes were found to be inappropriate for use in non-invasive or transthoracic cardiac imaging. This is primarily because the acoustical energy generated by the small transducers of invasive imaging probes is insufficient to penetrate the body and intervening anatomical structures.

Conventional transthoracic ultrasound imaging probes are generally elongated probes having an ultrasound transducer located on the distal end of the probe body. Typically, the probe is maneuvered so that the array of sensors is positioned adjacent to an imaging window on the patient to obtain a desired image of the cardiac functions and structures.

There are four primary echocardiographic imaging windows: the suprasternal, subcostal, parasternal and apical windows. The appropriateness of each imagining window depends upon the structures, functions and conditions to be diagnosed as well as the type and size of the patient. Each imaging window provides the opportunity to image a specific portion or characteristic of the cardiac structures and/or functions depending upon the portion of the heart which is nearest the imaging window, the angle of the probe at that window, and the intervening structures which may interfere with the image. In addition, the utility of certain windows is limited by the size and condition of the patient. Accordingly, specific windows are used to diagnose specific conditions and disorders of specific patients. For example, the subcostal window provides superior imaging of cardiac functions and structures of pediatric patients that cannot be achieved through the parasternal or apical windows. The subcostal window is the optimal window to achieve imaging of the superior mediastinum and outflow portions of left and right ventricles. For adult patients, the parasternal window is preferred. The subcostal window does not provide sufficient cardiac imaging of adult patients due to the distance between the windows and the heart and the development of the intervening anatomical structures in adults.

Conventional ultrasound imaging probes have been found to produce insufficient images at the suprasternal and subcostal windows, particularly in certain patients, primarily due to the inability to properly position the probe. To position a conventional ultrasound imaging probe at the suprasternal window, the patient must adjust his or her head back to avoid interference between the face and chin and the probe. Typically, this tilting is accomplished by placing an object, such as a pillow, behind the shoulders of an inclined patient, leaving his/her head unsupported. The patient then tilts his/her head backwardly until it reaches the surface supporting the body.

However, the neck of certain patients, such as children, is too small to accommodate the conventional ultrasound probes even while the patient's head is tilted. In addition, it is often difficult and uncomfortable for the patient to maintain his/her head in this awkward position during the echocardiographic procedure, particularly if the procedure is lengthy. As a result, it is not uncommon for the patient to move, reducing the quality of the resulting image. Furthermore, certain patients are unable to adjust their head as necessary to enable the conventional probe to access the suprasternal window. These patients include, for example, patients with neck and spinal injuries, patients with head trauma, convalescent and bedridden patients, etc. Using the suprasternal echocardiographic imaging window with these patients is virtually impossible.

Performing echocardiography using the subcostal window is particularly useful because the ultrasound imaging probe may image the heart without the rib cage or other bone structures interfering with the ultrasound image. To clear the sternum, the probe must be placed relatively far into the rib cage. In order to place a conventional probe at the subcostal window, the probe must be held substantially parallel with the patient's body. In this position, the sonographer cannot get his or her hands underneath the probe and therefore has a difficult time controlling the probe. As a result, sonographers typically attempt to maneuver the probe by holding it at the top, which is very difficult to do and causes considerable patient discomfort. This technique adversely affects the sonographer's ability to image the area of interest.

What is needed, therefore, is an ultrasound imaging probe that enables a sonographer to perform echocardiography using the suprasternal window without requiring a patient to move his/her head to permit the sonographer to properly position the probe. The probe should also be capable of providing imaging of the heart from the subcostal window without the need to use a hand or instrument to create the necessary space to place the imaging probe.

SUMMARY OF THE INVENTION

The present invention relates generally to an ultrasound imaging probe having connected tip and handle regions, each of which has a longitudinal axis that intersects the axis of the other at an acute angle. An ultrasonic transducer opposes a patient-contacting surface at a distal end of the tip region and is positioned orthogonally to that region's axis.

This novel shape enables the administering sonographer to position the probe at the suprasternal window without tilting the probe and without requiring the patient to adjust his/her head, thereby obtaining improved cardiac imaging of pediatric patients, patients with spinal injuries, and others who cannot steadily hold his/her head in a backwardly-tilted position to accommodate the placement of conventional ultrasonic probes. In addition, the shape allows for the unassisted positioning of the probe within the subcostal window, which is the preferred imaging window for performing echocardiography therapy on pediatric patients.

In one embodiment, the ultrasound transducer is a phased-array transducer rotatable about the tip region axis. An angled drive shaft having a universal joint transfers a rotational force generated in the handle region to the angled offset tip, rotating the transducer about the tip region axis with minimal rotational and radial forces. Advantageously, this embodiment enables the probe to be used to obtain multiple images from the same perspective without having to adjust the position of the probe on the patient. In addition, this embodiment results in a probe having a minimal number of lightweight parts associated with the rotation of the transducer. Advantageously, internally rotating the transducer behind a stationary patient-contacting surface prevents the probe from "walking" out of the narrow imaging window which would otherwise result in a loss of the desired image. In addition, this arrangement prevents pediatric patients from feeling the disconcerting rotation, enabling them to remain cooperative during the procedure.

In another embodiment, a strain-relief connector assembly having a flex circuit, an angled flex circuit holder and an energy-absorbing coax bundle, provide electrical connections about the periphery of the probe between a cable connected to the proximal end of the handle region and the ultrasound transducer at the distal end of the structure. As the flex circuit and flex circuit holder rotate with the transducer, the holder maintains a secure electrical connection between the coax bundle and flex circuit while the coax bundle absorbs the energy associated with the rotation. This arrangement prevents electrical connection failures from occurring during repeated rotations. Specifically, the coax bundle contains individually-insulated coax wires, the number of which preferably corresponds to the number of sensor elements in the ultrasound transducer. Alternatively, there may be additional wires in the coax bundle to support other types of sensors in the probe. The coax wires are restrained only at specific locations along their length, leaving them free to move as the flex circuit rotates.

Further features and advantages of the present invention as well as the structure and operation of various embodiments of the present invention are described in detail below with reference to the accompanying drawings. In the drawings, like reference numerals indicate identical or finctionally similar elements. Additionally, the left-most one or two digits of a reference numeral identifies the drawing in which the reference numeral first appears.

BRIEF DESCRIPTION OF THE DRAWINGS

This invention is pointed out with particularity in the appended claims. The above and further advantages of this invention may be better understood by referring to the following detailed description when taken in conjunction with the accompanying drawings, in which:

DETAILED DESCRIPTION

Figure 1:
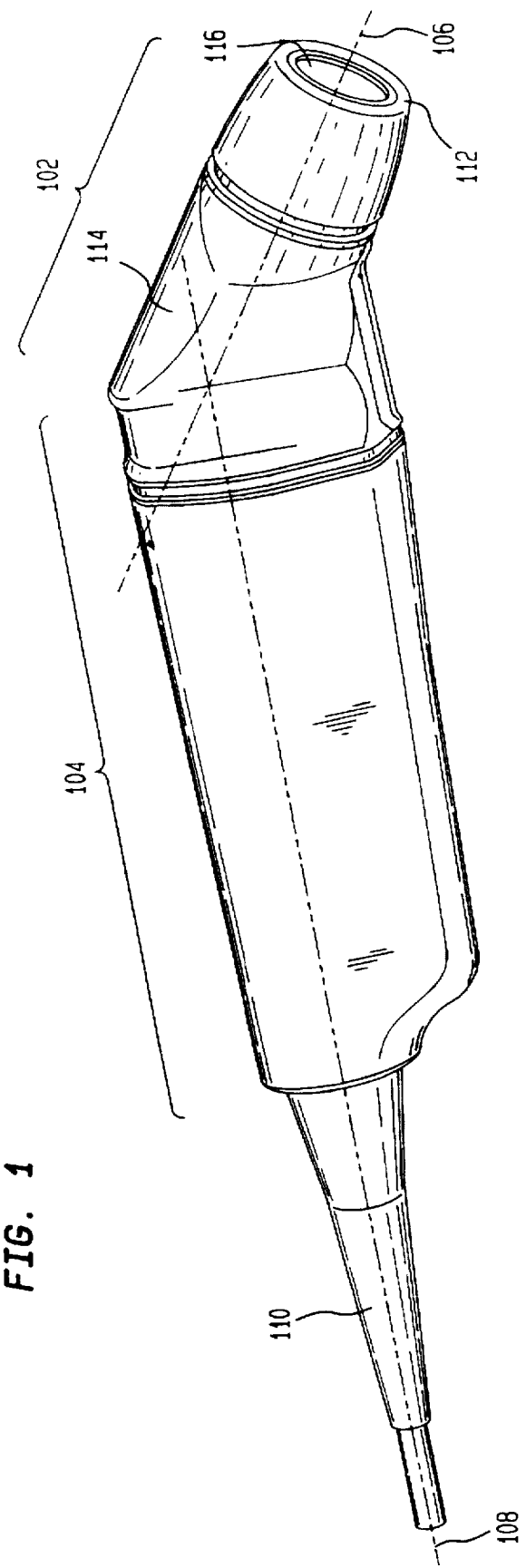
FIG. 1 is a perspective view of one embodiment of the ultrasound imaging probe of the present invention.

A perspective view one preferred embodiment of the ultrasound imaging probe of the present invention is illustrated in FIG. 1. The ultrasound imaging probe 100 includes a tip region 102 and an integral handle region 104. The handle region 104 has a longitudinal axis 108 extending from its proximal to distal end. Likewise, tip region 102 has a longitudinal axis 106 extending from its proximal end to its distal end. At the distal end of the tip region 102 is a patient-contacting surface 112. The patient-contacting surface 112 lies in a plane that is orthogonal to longitudinal axis 106 of tip region 102. An ultrasound transducer (not shown in FIG. 1) lies within the tip region 102 opposing the patient-contacting surface 112. The tip and handle regions 102 and 104 are connected to each other at their proximal and distal ends, respectively. Longitudinal axes 106 and 108 lie in the same plane and intersect each other at an acute angle 114 as illustrated in FIG. 1. That is, the tip region 102 is offset at an acute angle with respect to the handle region 104. Alternatively, the tip region 104 may be offset from the handle region 104 such that the longitudinal axis 106 intersects, but does not reside in the same plane as the longitudinal axis 108.

The dual-sectioned ultrasonic transducer probe 100 with an offset, angled tip section 102 having an orthogonal ultrasound transducer at its distal end enables an administering sonographer to position the ultrasound transducer at a patient's subcostal window without significantly tilting the probe. In addition, the angled offset tip section 102 enables the sonographer to easily obtain cardiac images at the subcostal window without having his or her hand captured between the probe and patient abdomen which would inhibit further angulation of the probe. As a result, significantly improved cardiac images are obtained with the ultrasound imaging probe 100 of the present invention. This offset angle also enables easy access at the suprasternal window without requiring the patient to significantly adjust his/her head. This particularly helpful for pediatric and other patients who cannot tilt their heads backwards for an extended period of time to accommodate conventional ultrasonic probes, and who require the echocardiography to be performed at the suprasternal window.

As described below, the ultrasound transducer is preferably a small, phased-array transducer. Accordingly, the patient-contacting surface 112 includes a small imaging window 116 through which the ultrasound energy is transferred. The reduced size of the transducer enables it to be positioned orthogonal to the tip region axis 106. This limited surface area of the ultrasound transducer that must be positioned at the echocardiographic imaging window enables the administering sonographer to hold the probe 100 such that only the patient-contacting surface 112 contacts the patient. This small imaging window provides significantly increased access to the suprasternal and subcostal windows for performing transthoracic ultrasound imaging.

As will be explained in detail below, a majority of the functional components of probe 100 are located in the handle region 104, enabling the tip region 102 to have a relatively short length. This short tip region 102 is then coupled to the handle region 104 at an acute angle 114, with the mechanical and electrical functions adjusted to accommodate this non-linear arrangement. In one embodiment of the present invention, acute angle 114 is preferably in the range of 20° to 50°. In another embodiment, the range of angle 114 is 15° to 60°. In yet another embodiment, angle 114 is in the range of 30° to 40°. In still another embodiment of the present invention, angle 114 is approximately 35°.

The handle region 104 is connected to a cable 110 through which the probe 100 is electrically coupled to a conventional ultrasound control and display system (not shown). In a preferred embodiment, the control and display system controls the operation of the probe 100 and receives and processes imaging signals generated by the probe transducer. The resulting images are then displayed on a display for use by the sonographer during and after the echocardiographic procedure.

Figure 2:
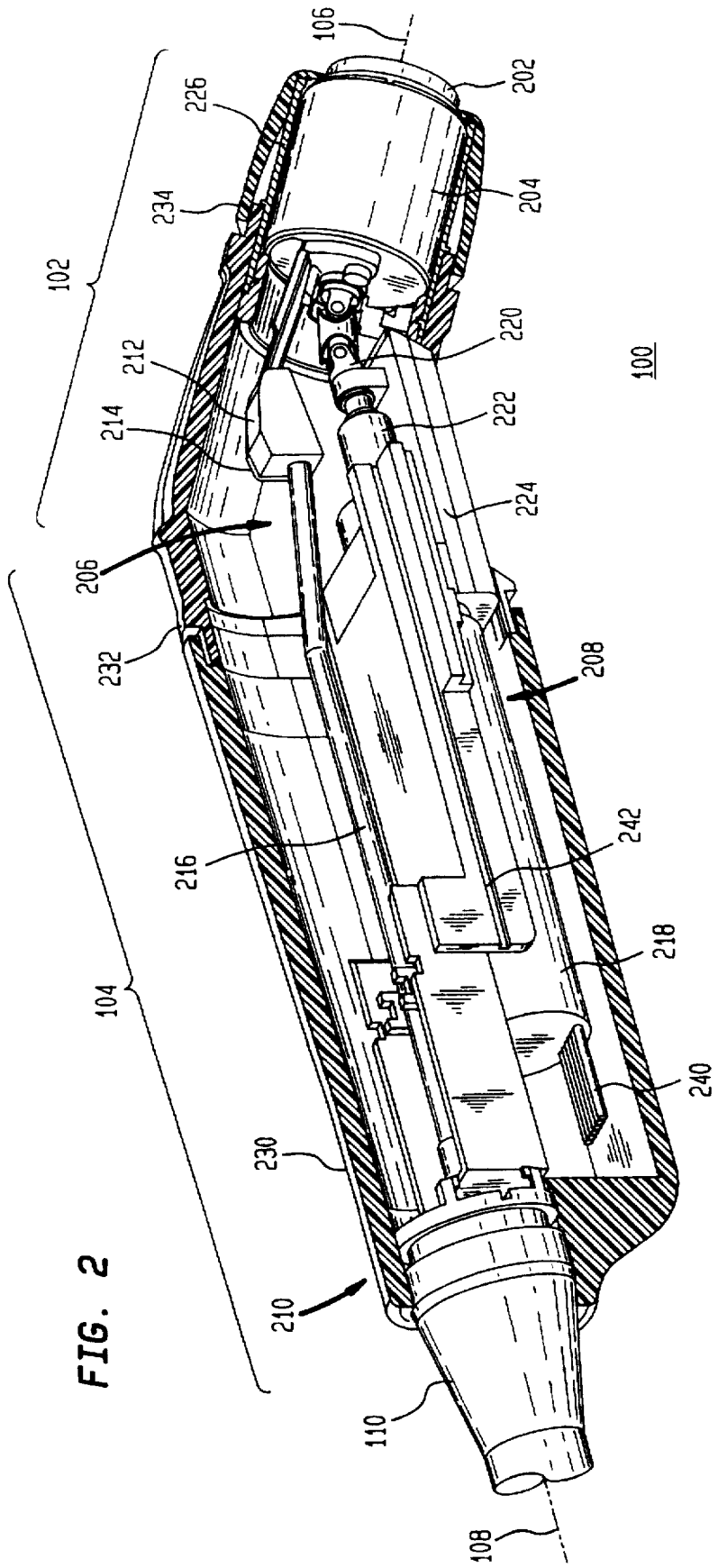
FIG. 2 is an exposed regional view of the ultrasonic probe of FIG. 1.

FIG. 2 is a sectional view of the ultrasound probe 100. Generally, the probe 100 includes a number of functional components or assemblies. An ultrasound transducer 202 is housed within tip region 102. A drive mechanism 208 rotates the transducer 202 in response to commands received through cable 110. A strain-relief connector assembly 206 electrically couples the transducer 202 to the cable 110. These probe assemblies are removably secured in sleeve casing 210.

The ultrasound transducer 202 is preferably a phased-array transducer rotatable about the tip region axis 106. The imaging lens of the transducer is essentially disposed orthogonally to the longitudinal axis 106, providing a field of view extending from the distal end of the tip region 102 which is essentially symmetrical about the longitudinal axis 106. The transducer 202 is disposed substantially parallel with the imaging window 116 of the patient-contacting surface 112. Preferably, the transducer 202 is adjacent to the window 116, separated only by a fluid layer to avoid damage to the transducer and window during rotation as well as to couple acoustic energy to the window.

The drive mechanism 208 includes a motor 218, a drive shaft 220, and a keyed coupler 222 for connecting the two, all of which are mounted on a drive mechanism support base 224. The drive shaft 220 is connected to a rear surface of a preferably cylindrical journal 204. The front surface of the journal is connected to the transducer 202. As described below, rotational forces generated by motor 218 are transferred to the transducer 202 via the drive shaft 220, coupler 222 and journal 204. The motor 218, drive shaft 220 and coupler 222 are mounted on, and supported by, a drive mechanism support base 224. The coupling of the drive shaft 220 and the journal 204 is achieved through a bearing and bearing coupler (described below with reference to FIGS. 3 and 4). The journal 204 is supported by a bushing 226 which permits rotation about the longitudinal axis 106. The drive shaft 220 will be described in detail below with reference to FIG. 3.

A strain-relief connector assembly 206 maintains a secure electrical connection between the cable 110 and the transducer 202 during repeated rotations of the transducer 202. The strain-relief connector assembly 206 includes a flex circuit 212, an angled flex circuit holder 214 and an energy-absorbing coax bundle 216, together providing electrical connections about the periphery of the probe 100 between the cable 110 connected to the proximal end of the handle region 104 and the ultrasound transducer 202 at the distal end of the tip region 102.

The flex circuit 212 includes a number of leads, one connected to each sensor element of transducer 202. The flex circuit 212 extends through the journal 204 to the rear surface of the journal 204. The flex circuit holder 214 is mounted on the rear surface of the journal 204 via screws or other mounting means. The flex circuit holder 214 provides a secure and stable surface for connecting the flex circuit 212 to an energy-absorbing coax bundle 216. The portion of the flex circuit 212 that extends through the rear surface of journal 204 is secured to the flex circuit holder 214.

The coax bundle 216 contains a number of coax wires that are individually insulated and secured only at predetermined locations along their length so that the coax bundle 216 can travel with the rotation of journal 204 while maintaining minimum strain on the electrical connections. Preferably, the individual wires of coax bundle 216 are connected to the flex circuit 212 and the flex circuit holder 214 at their distal end and are secured to the probe at locations necessary to minimize the energy state of the cable. Preferably, the coax wires are soldered to the flex circuit 212. However, other means for securing the coax wires to the flex circuit 212 may be used. For example, heat shrink tubing, adhesive tape or mechanical clamping may be used. The coax bundle 216 is secured near its proximal end by adhesive tape or mechanical clamping to a probe structure prior to connecting to cable 110. Alternatively, the cable may also be slidingly held to a probe structure at one or more intermediate locations along its length. Such additional securing means may be necessary to maintain the cable at a minimum energy state. Like the leads of flex circuit 212, the number of coax wires contained in coax bundle 216 preferably corresponds to the number of sensor elements in ultrasound transducer 202. In one embodiment of the present invention, transducer 202 is comprised of 64 sensor elements. Accordingly, flex circuit 212 has 64 leads and coax bundle 216 has 64 wires.

As described below, the drive mechanism 208 transmits rotational force to the journal 204 via the longitudinal axes 108 and 106 to rotate the transducer 202 about longitudinal axis 106. Accordingly, the strain-relief connector assembly 206 must provide electrical connection between the cable 110 and the transducer 202 via the periphery of tip region 102 of the probe 100. Thus, the flex circuit holder 214 is mounted to the rear surface of journal 204 such that it extends from the periphery of the journal. In addition, the flex circuit holder 214 is shaped so as to provide access to the flex circuit 212 at the periphery of the proximal end of the tip region 102. Accordingly, the coax bundle 216 extends axially along the length of the handle region 204 above the drive mechanism 208 to join the flex circuit 212 at the flex circuit holder 214. In the same manner, the coax bundle 216 is connected to the proximal end of handle region 104 at a point that is substantially aligned with the coax bundle 216.

The strain-relief connector assembly 206 securely connects the transducer 202 with the cable 110. The flex circuit holder 214 and the coax bundle 216 prevent electrical connection failures from occurring due to repeated rotations of the journal 204 during the operation of the probe 100. This is because the coax bundle 216 is minimally restrained and easily travels with the flex circuit holder 214 as the journal 204 is rotated by drive mechanism 208. The unrestrained individually insulated wires of the coax bundle 216 absorb the energy that is generated from this rotation; the end connections at flex circuit holder 214 and cable 110 are therefore minimally strained.

Figure 3:
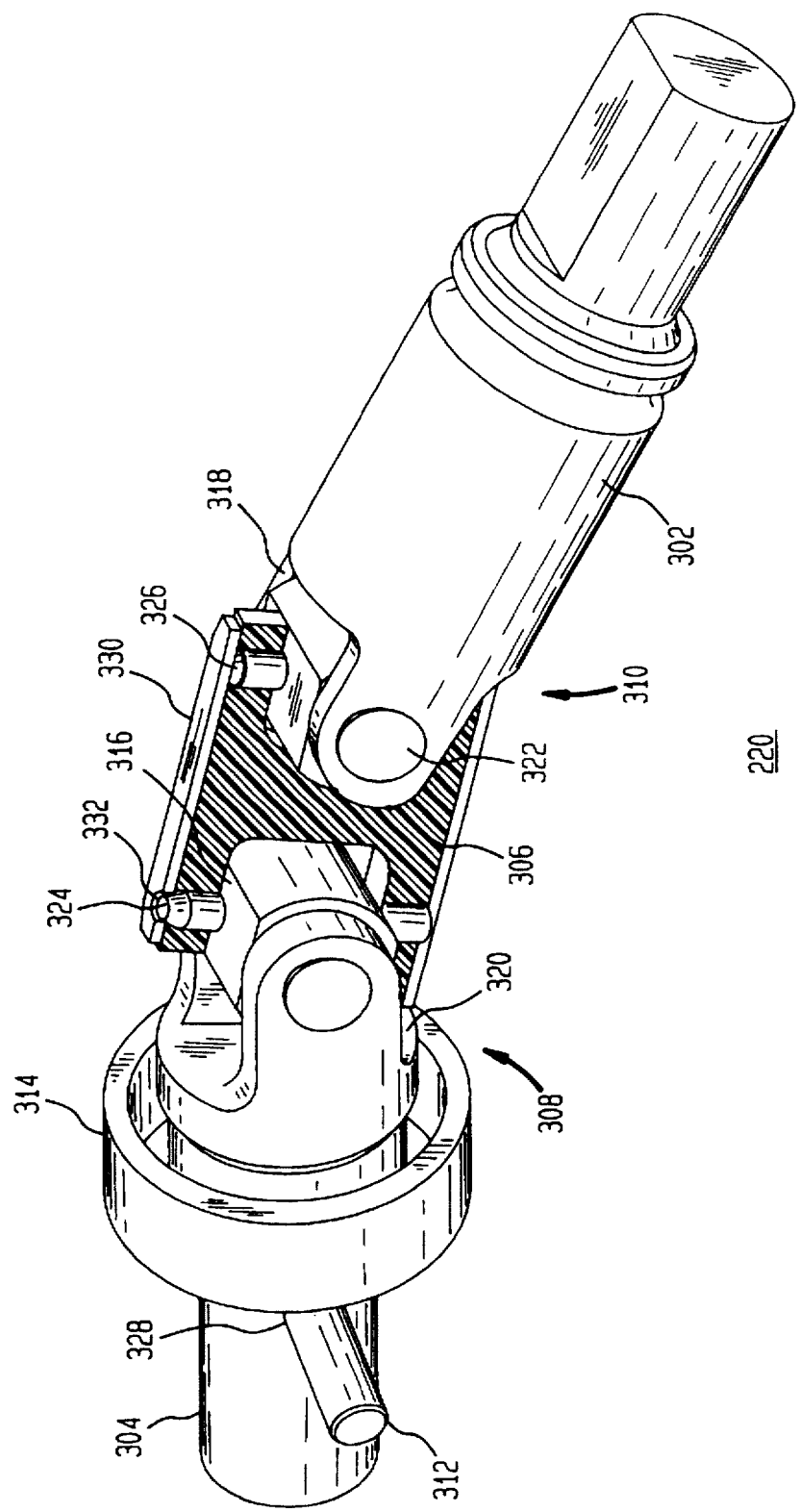
FIG. 3 is a perspective view of a drive shaft of an ultrasonic probe according to the present invention.

A perspective view of drive shaft 220 is illustrated in FIG. 3. In one embodiment of the present invention, drive shaft 220 includes an input shaft 302, an output shaft 304 and an intermediate shaft 306 connected to output shaft 304 and input shaft 302 via U-joints 308 and 310, respectively. The drive shaft 220 is preferably angled to transfer a rotational force generated by the motor 218 in the handle region 104 to the angled offset tip region 102. The drive shaft 220 rotates the transducer 202 about the tip region axis 106, enabling the probe 100 to be used to obtain multiple images from the same perspective without having to adjust the position of the probe on the patient. In addition, this arrangement results in a probe having a minimal number of lightweight parts associated with the rotation of the transducer 202.

The output shaft 304 has a cross hole 328 configured in its side to receive a drive pin 312. The rear surface of the journal 204 has a T-shaped locking channel located on the longitudinal axis 106 for receiving the distal end of the output shaft 320 of the drive shaft 220 and to engage the drive pin 312 to rotationally secure the drive shaft 220 to the journal 204. A ball bearing 314 having inner and outer races is rotationally and axially secured to the output shaft 304. Likewise, the journal 204 is connected to the inner race of the ball bearing 314. Thus, the inner race rotates with the drive shaft 220 and journal 204.

The universal joints 308 and 310 include universal joint couplers 316 and 318, respectively, removably secured to output shaft 304 and input shaft 302 via large cross pins 320 and 322, respectively. The large cross pins 320 and 322 have cross holes that align with corresponding cross holes in universal joint couplers 316 and 318. These corresponding cross holes are aligned to receive cross pins 324 and 326, respectively. A drive shaft sleeve 330 removably secures cross pins 324 and 326 in position, thereby securing all the components of drive shaft 220.

As shown in FIG. 3, sleeve 330 has an orifice 332 for receiving a tapered top portion of cross pin 324. Cross pin 326 is of shorter length and does not include a tapered region. During assembly, the sleeve 330 is slid over the cross pin 326 since it has a length that it does not obstruct the passage of the sleeve 330. The tapered portion of the cross pin 324, however, extends beyond the upper surface of intermediate shaft 306. As sleeve 330 passes over the cross pin 324, it is flexed outward over the tapered portion. When the sleeve is advanced such that the orifice 332 is aligned with the top of the cross pin 324, the sleeve contracts to its natural shape such that the tapered end of the cross pin 324 resides in the orifice 332. To disassemble the drive shaft 220, the cross pin 324 is simply pushed down against opposite side of the sleeve 330 which flexes in response to the force of the cross pin to disengage the sleeve 330. The sleeve 330 may then be slid over the cross pin 326 and removed from the drive shaft 220. The cross pins may then be removed and the universal joints and drive shaft disassembled. Thus, all of the components of drive shaft 220 are held together with four cross pins 320–326 and sleeve 330 which may be easily removed to repair or maintain the drive shaft 220. It should be noted that both sides of the cross pin 324 as well as either or both sides of cross pin 326 may also be tapered. The sleeve 330 would then be configured with appropriately-aligned orifices to capture the tapered pins.

The drive shaft 202 transfers the rotational force generated by motor 218 around the angle 114 between the handle region 104 and tip region 102 of probe 100. The drive shaft 220 transfers this rotational force along the center axis of the drive shaft thereby minimizing the radial forces associated with such rotation. As a result, there is no requirement to employ a sophisticated bearing system to support the rotational forces generated by motor 218. Therefore, as shown in FIG. 2, journal 204 only requires bushing 226 to support its rotation. Thus, the drive shaft 220 of the present invention has a simple, easily-maintainable structure that transfers rotational forces while creating minimal radial forces. A fluid may be interposed between the journal 204 and bushing 226 to reduce the friction generated by the radial forces.

In one embodiment of the present invention, the drive shaft 220 is a constant velocity drive shaft. That is, the rate of change of rotation experienced by output shaft 304 is substantially the same that experienced by the input shaft 302. This is due to the three-jointed segments 302, 304 and 306 connected through universal joints 308 and 310 as described above. As a result, the control system (not shown) that commands motor 218 knows the degree of rotation of transducer 202, enabling it to create multiple-dimensional images based upon the returned image signals from transducer 202. In an alternative embodiment, the drive shaft 220 is a two-segment variable velocity drive shaft. In such an embodiment, the output shaft 304 is directly coupled to the input shaft 302. The relationship between the output shaft 304 and input shaft 302 is well known and easily determinable given the angle between the input and output shafts.

Casing 210 preferably includes three interlocking sleeves: probe handle sleeve 230, tip handle sleeve 232 and tip sleeve 234. The tip handle sleeve 232 has ledges on its proximal and distal ends for interlocking with corresponding surfaces on tip sleeve 234 and probe handle sleeve 230. The seal between the three casing sleeves is accomplished with either RTV, epoxy, or some other known sealant. The cable 110 has a cable bushing that cooperates with a rear orifice at the proximal end of the handle region 104. A seal is typically maintained through the use of a radial O-ring.

The interlocking sleeves of the casing 210 provide a complete seal around the probe 100. In addition, the seals are positioned so that they are not exposed to the touch of the administering sonographer. The streamline nature of the probe 100 in conjunction with this casing arrangement makes the probe 100 of the present invention ergonomically advanced over conventional ultrasound probes. For example, some conventional probes typically use a clam shell housing. The seam between the two clam shell housings runs the length of conventional probes and is distracting to the administering sonographer. In addition, even the slightest variations are difficult to seal.

To avoid damage to the fragile transparent window 116, the probe 100 is preferably manufactured in two separate assemblies that are themselves later assembled. The tip casing 234, the bushing 226 and the window 116 are preferably manufactured as a separate assembly. To secure this assembly to the remaining portion of the probe 100, the bushing 226 is simply threaded onto the bearing coupler (discussed below). This ensures that the window 116 is not exposed to potential damage during manufacturing or shipping and further ensures that, should the window be damaged during the use of the probe 100, it may be replaced quickly and easily.

A chassis 240 is connected to the proximal end of the drive mechanism support structure 224, typically with screws. Chassis 240 has two side channels 242 for engaging an RFI shield. The RFI shield (not shown) and the chassis 240 together form a complete RFI shield, protecting the cable bundle 216 from interference, thereby minimizing noise in the resulting image. The coax bundle 216 is secured to the chassis with a small amount of slack in the cable so as to accommodate the rotational movement of the journal 204 without placing stress on the bundle itself as described above. A printed circuit board (PCB; not shown) is attached to the underside of the chassis 240 for assisting in the transfer of signals through the probe 100.

Figure 4:
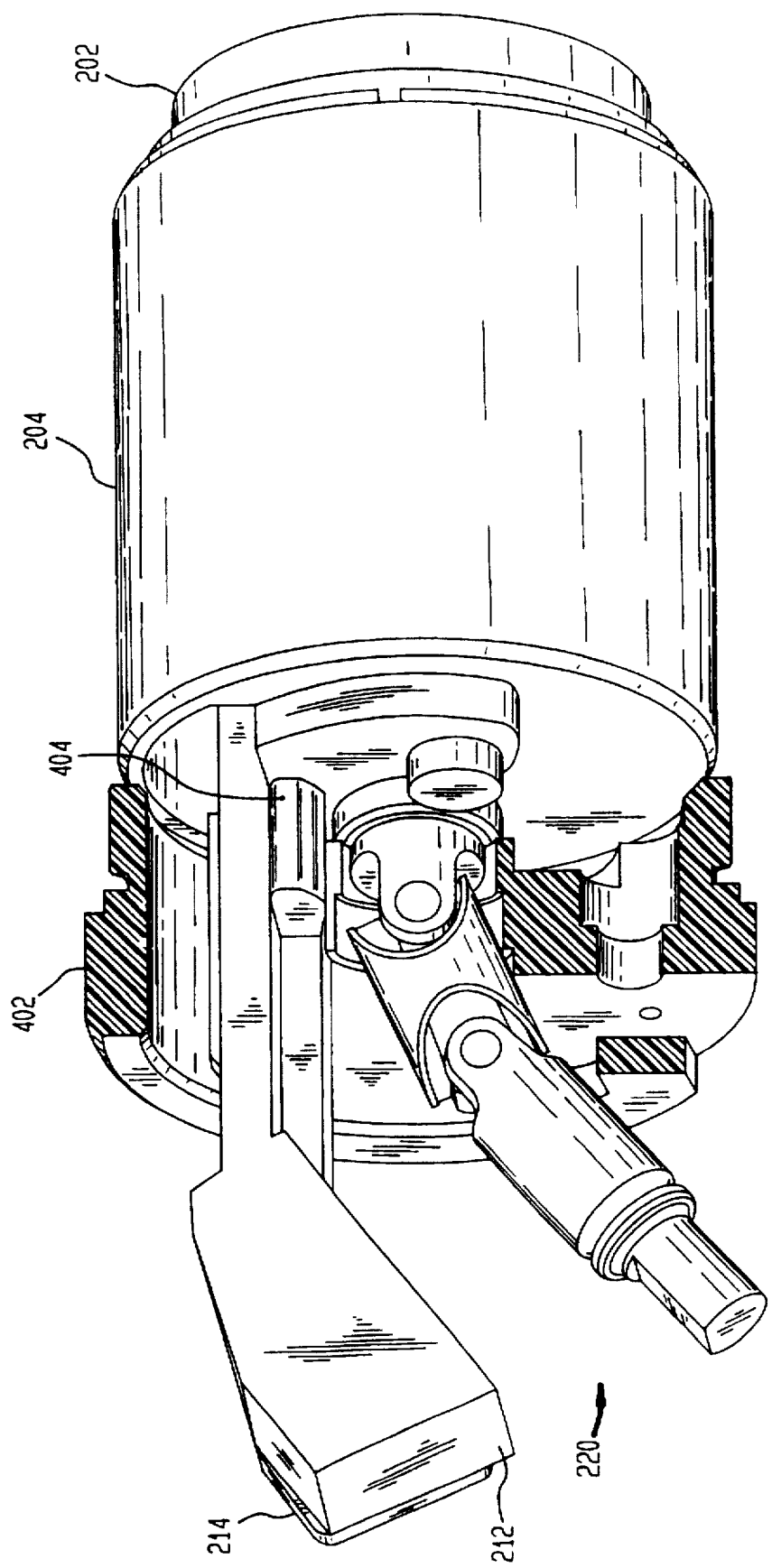
FIG. 4 is a rear perspective view of the journal, drive shaft, flex circuit, and a regional view of the bearing coupler of an ultrasonic imaging probe according to the present invention.

FIG. 4 is a rear perspective view of journal 204 showing drive shaft 220, flex circuit holder 214 and a bearing coupler 402. The bearing coupler 402 supports the transfer of rotational force from the drive shaft 220 to the journal 204 and controls the degree of rotation of journal 204. The bearing coupler 402 is a cylindrical or annular member positioned adjacent to the rear surface of the journal 204. The bearing coupler 402 has thread on its anterior surface at its distal end for receiving bushing 226.

The bearing coupler 402 is rotationally secured to the outer race of the drive shaft bearing 314, holding the outer race stationary as the inner race of the bearing 314 rotates with the drive shaft 220. Thus, as the drive shaft 220 rotates, the inner race of bearing 314 follows the drive shaft rotation while the outer race of bearing 314 remains stationary. Since the drive shaft 220 is lockingly engaged with the rear surface of the journal 204, the rotational force generated by motor 218 is transferred to the journal 204 supported by bearing 314 and bushing 226, causing the journal 204 to rotate in bushing 226 (shown in FIG. 2).

To control the degree of rotation of the journal 204, the bearing coupler 402 includes end stops (shown in FIG. 5) integral with the outer race of bearing 314. The bearing coupler end stops interoperate with corresponding end stops on the flex circuit holder 214. One journal end stop 404 is shown in FIG. 4 on the flex circuit holder 214. The other journal end stop on the opposite side of the flex circuit holder 214 is not shown. Since the bearing coupler 402 does not rotate with the flex circuit holder 214, the bearing coupler and journal end stops define the allowable angular travel of journal 204. In addition to securing the outer race of bearing 314 and providing a limited range of travel of drive shaft 220, the bearing coupler 402 provides a configured surface on its proximal end onto which the drive mechanism support structure 224 attaches.

Figure 5:
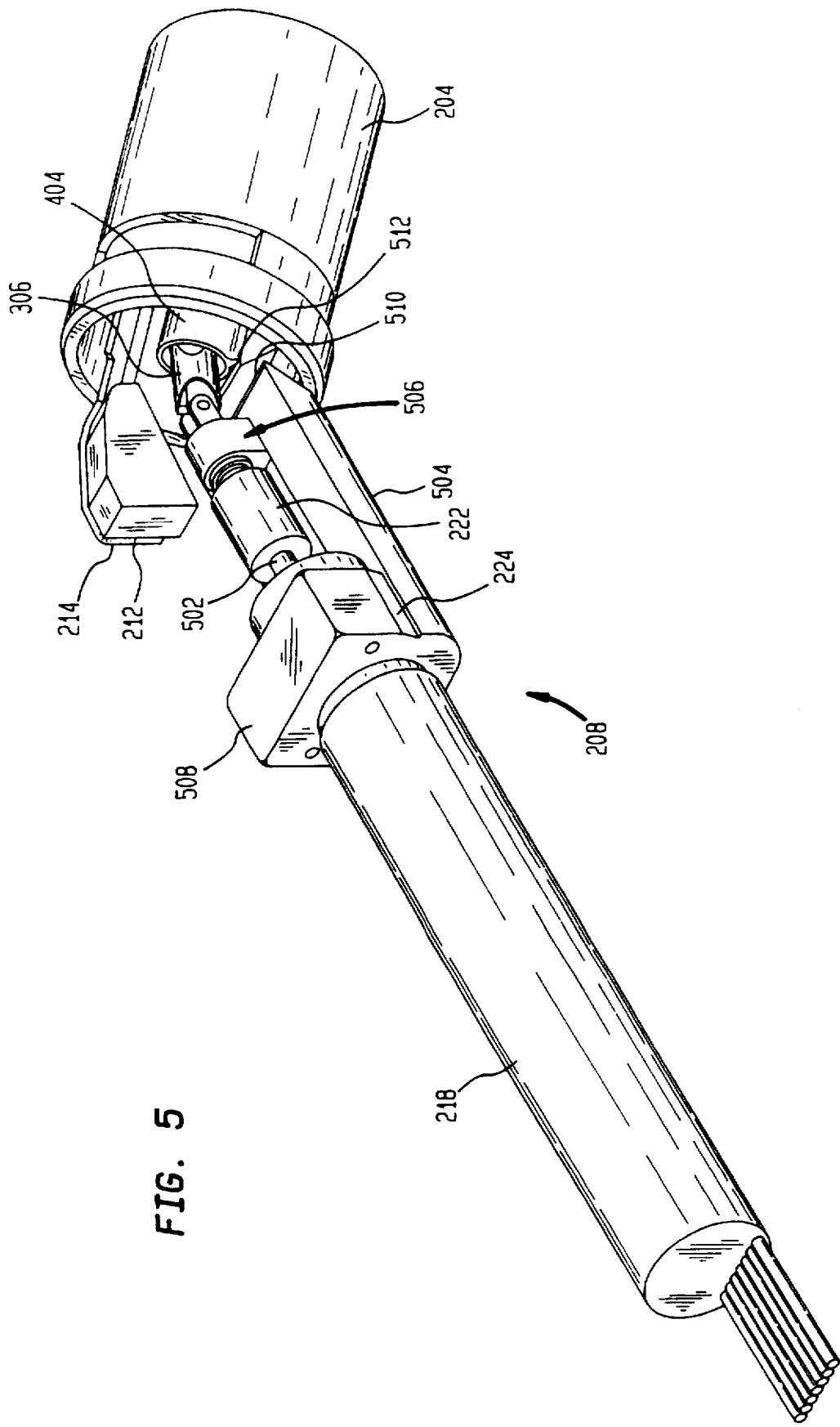
FIG. 5 is a rear perspective view of a drive mechanism of an ultrasonic imaging probe according to the present invention.

FIG. 5 is a rear perspective view of probe 100 with the casings removed showing the components of the drive mechanism 208. The drive mechanism support base 224 is connected to the bearing coupler 402 and provides a support structure for drive shaft 220, motor 218 and coupler 222. The drive mechanism support base 224 rotationally secures these drive mechanism assembly components in fixed axial relationship with each other. Drive mechanism support base 224 includes an angled base portion 502 having two integral segments. A forward segment 510 connects the drive mechanism support base 224 to the bearing coupler 402. The rear segment 504 is integral with the front segment 510 at an angle accommodating the angular relationship between the drive shaft 220 and journal 224. The rear base portion 504 has an upper surface with an integral drive shaft holder 506 for slidably securing the input shaft 302 of the drive shaft 220, axially securing the drive shaft 220 relative to the motor 218. A motor holder 508 integral with the upper surface of the rear base portion 504 is configured to receive and axially secure the motor 218 with respect to the drive shaft 220.

The drive shaft coupler 222 couples the input shaft 302 with the shaft 502 of motor 218. The coupler 222 has, through its center, a keyed cut-out, each end of which engages the appropriately-shaped motor output shaft 502 and input shaft 302. Thus, the components of the entire drive mechanism 208 are secured together without the use of adhesives, fittings, or other permanently-securing means. The rotational force generated by motor 218 is transferred from the motor output shaft 502 to the drive shaft 220 via coupler 222 causing the drive shaft to rotate which in turn causes the journal 204 and transducer 202 to rotate. The journal 204 rotates until end stops 404 and 512 contact each other.

During operation, the administering sonographer places the patient contacting surface 112 against an echocardiographic imaging window such as the subcostal or suprasternal imaging windows. To properly position the window 116 at the suprasternal window, the administering sonographer simply places the surface 112 against the patient with the patient having to adjust his/her head in any way to accommodate the probe 100. The sonographer or another activates the control system (not shown) that generates electrical commands to the motor 218 to cause the ultrasonic transducer 202 to rotate from one end of its range of motion to the other. The transducer 202 is required to travel 180° to obtain the maximum number of images. In one embodiment of the present invention, the journal and bearing coupler end stop described above are positioned such that the transducer 202 has a 190° range of travel. Significantly, this enables the probe 100 of the present invention to supply the necessary imaging data to perform three-dimensional echocardiography. In addition, this is achieved without requiring the sonographer to move the probe 100 during imaging.

At the subcostal window, the sonographer points the tip region 102 of the probe 100 upwardly and presses the upper surface of the sleeve 210 at the tip region 102 against the body below the sternum until the patient contacting surface 112 clears the sternum. Once the probe is in this positioned at its desired angle, the sonographer performs the echocardiographic procedure as described above.

As one skilled in the relevant art would find apparent, the probe 100 of the present invention may be used with other viewing windows, including the parasternal and apical windows. Furthermore, to perform imaging of body structures other than the heart, the probe 100 of the present invention may be utilized in like manner.

It is also noted that the ultrasound probe may be used in a wide variety of applications including the transthoracic application described above.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. An external ultrasonic imaging probe comprising:

a handle region having first distal and proximal ends and a first longitudinal axis;

a tip region having second proximal and distal ends, said second proximal end coupled to said first distal end, and a second longitudinal axis intersecting said first longitudinal axis at an acute angle, wherein said tip region includes a patient-contacting surface located at said second distal end with a substantially planar imaging window that is substantially orthogonal with said second longitudinal axis, and an ultrasound transducer adjacent to and substantially parallel with said imaging window to provide a field of view extending from said imaging window; and a drive mechanism configured to rotate said ultrasound transducer about said second longitudinal axis.

2. The probe of claim 1, wherein said ultrasound transducer is symmetrical about said second longitudinal axis.

3. The probe of claim 2, further comprising:

a strain-relief connector assembly configured to connect said ultrasound transducer and a cable connected to said proximal end of said handle region.

4. The probe of claim 3, wherein said strain-relief connector assembly comprises:

a flex circuit connected to a peripheral region of said ultrasound transducer;

a coax bundle, having a plurality of coax wires restrained to maintain said coax bundle in a minimum energy state, configured to connect said cable and said flex circuit; and a flex circuit holder for providing a point of connection between said coax bundle and said flex circuit.

5. The probe of claim 1, wherein said drive mechanism comprises:

a motor, residing in said handle region, configured to generate a rotational force;

an angled drive shaft, coupled to said motor and to said ultrasound transducer, configured to axially transfer said rotational force to said ultrasound transducer to cause said ultrasound transducer to rotate about said second longitudinal axis.

6. The probe of claim 5, wherein said an angled drive shaft comprises:

an input shaft;

an output shaft; and an intermediate shaft interposed between and connected to said input and output shafts with universal joints.

7. The probe of claim 6, wherein said angled drive shaft further comprises:

universal joint couplers, positioned at said universal joints, having through holes aligned with through holes in said shafts;

cross pins slidingly positioned within said through holes to join said shafts, at least one of said cross pins having a tapered end; and a flexible drive shaft sleeve having at least one orifice, each of which is configured to receive said tapered end of said at least one cross pin.

8. The probe of claim 1, wherein said acute angle is in the range of 20° to 50°.

9. The probe of claim 1, wherein said acute angle is in the range of 30° to 40°.

10. The probe of claim 1, wherein said acute angle is approximately 35°.

11. An external ultrasonic imaging probe comprising:

a handle region having first distal and proximal ends and a first longitudinal axis;

a tip region having a second proximal and distal ends, said second proximate end coupled to said first distal end, and a second longitudinal axis intersecting said first longitudinal axis at an acute angle, said tip region including, a patient-contacting surface located at said second distal end having a substantially planar imaging window that is substantially orthogonal with said second longitudinal axis, and an ultrasonic transducer adjacent to and substantially parallel with said imaging window, said ultrasound transducer rotatable about said second longitudinal axis; and means for rotating said ultrasound transducer about said second longitudinal axis.

12. The probe of claim 11, wherein said rotating means comprises:

means for generating said rotational force; and means for transferring said rotational force to said ultrasound transducer to cause said ultrasound transducer to rotate about said second longitudinal axis.

13. The probe of claim 12, wherein said means for generating a rotational force resides in said handle region.

14. The probe of claim 11, further comprising:

means for electrically connecting said ultrasound transducer and said means for generating a rotational force to an external control system.

15. The probe of claim 11, wherein said acute angle is in the range of 30° to 40°.

16. The probe of claim 11, wherein said acute angle is approximately 35°.

17. The probe of claim 11, wherein said tip and handle regions are integral regions of the probe.

18. The probe of claim 11, wherein said first and second longitudinal axes reside in the same plane.

19. An external ultrasonic imaging probe comprising:

a handle region having first distal and proximal ends and a first longitudinal axis;

a tip region having second proximal and distal ends, said second proximal end being coupled to said first distal end, and a second longitudinal axis intersecting said first longitudinal axis at an acute angle, said tip region including a patient-contacting surface located at said second distal end with a substantially planar imaging window that is substantially orthogonal with said second longitudinal axis, and an ultrasound transducer adjacent to and substantially parallel with said imaging window to provide a field of view extending from said imaging window;

a drive mechanism, including a motor configured to generate a rotational force and an angled drive shaft configured to axially transfer said rotational force to said ultrasound transducer to cause said ultrasound transducer to rotate about said second longitudinal axis; and a strain-relief connector assembly configured to electrically connect said ultrasound transducer to an external cable at said proximate end of said handle region, said assembly including a flex circuit connected to said ultrasound transducer, an energy-absorbing coax bundle restrained at predetermined locations along its length, and a flex circuit holder for providing a point of connection between said coax bundle and said flex circuit.

* * * * *